(12) United States Patent
Swennen et al.

(10) Patent No.: US 11,517,439 B2
(45) Date of Patent: Dec. 6, 2022

(54) BIORESORBABLE BONE IMPLANT AND PRODUCTION METHOD

(71) Applicant: KARL LEIBINGER MEDIZINTECHNIK GMBH & CO. KG, Mühlheim (DE)

(72) Inventors: Gwenn Swennen, Knokke (BE); Frank Reinauer, Emmingen-Liptingen (DE); Tobias Wolfram, Dreieich (DE); Adem Aksu, Schwenningen (DE)

(73) Assignee: Karl Leibinger Medizintechnik GmbH & Co. KG, Mühlheim (DE)

( * ) Notice: Subject to any disclaimer, the term of this patent is extended or adjusted under 35 U.S.C. 154(b) by 0 days.

(21) Appl. No.: 16/629,278

(22) PCT Filed: Jul. 10, 2018

(86) PCT No.: PCT/EP2018/068659
§ 371 (c)(1),
(2) Date: Jan. 7, 2020

(87) PCT Pub. No.: WO2019/011913
PCT Pub. Date: Jan. 17, 2019

(65) Prior Publication Data
US 2020/0188119 A1 Jun. 18, 2020

(30) Foreign Application Priority Data
Jul. 10, 2017 (DE) ...................... 10 2017 115 403.5

(51) Int. Cl.
*A61F 2/28* (2006.01)
*A61F 2/30* (2006.01)

(52) U.S. Cl.
CPC ........ *A61F 2/2803* (2013.01); *A61F 2/30942* (2013.01); *A61F 2002/30011* (2013.01);
(Continued)

(58) Field of Classification Search
CPC ................ A61F 2/2803; A61F 2/30942; A61F 2002/30011; A61F 2002/30062;
(Continued)

(56) References Cited

U.S. PATENT DOCUMENTS 5,769,637 A 6/1998 Morgan
5,976,149 A * 11/1999 Masini .................. A61F 2/4684
606/91

(Continued)

FOREIGN PATENT DOCUMENTS

CN 106580520 4/2017
DE 199 15 395 10/2000
(Continued)

OTHER PUBLICATIONS

International Search Report and Written Opinion from International Application No. PCT/EP2018/068659 dated Sep. 14, 2018.
(Continued)

*Primary Examiner* — Bruce E Snow
(74) *Attorney, Agent, or Firm* — Beyer Law Group LLP (57) ABSTRACT

The invention relates to a bone implant (1) for correcting an incorrect position of a bone, the bone implant (1) having a first portion (2) for attachment to a first bone portion (3) and a second portion (4) for attachment to a second bone portion (5), the bone implant (1) being prepared so that, when fixed to the bone, it orients the first bone portion (3) and the second bone portion (5) with respect to one another and keeps said portions at a distance from one another, the bone implant (1) having such a geometry and being adapted so as to force a predetermined orientation of the second bone portion (5) relative to the first bone portion (3). The invention also relates to a method for producing such a bone implant (1).

15 Claims, 5 Drawing Sheets

(52) U.S. Cl.
CPC .............. *A61F 2002/30062* (2013.01); *A61F 2002/3092* (2013.01); *A61F 2002/30962* (2013.01); *A61F 2310/00017* (2013.01); *A61F 2310/00041* (2013.01); *A61F 2310/00293* (2013.01); *A61F 2310/00365* (2013.01)

(58) Field of Classification Search
CPC .... A61F 2002/3092; A61F 2002/30962; A61F 2310/00017; A61F 2310/00041; A61F 2310/00293; A61F 2310/00365; A61F 2002/2807; A61C 13/0013; A61C 8/0006
See application file for complete search history.

(56) References Cited

U.S. PATENT DOCUMENTS

| | | | |
|---|---|---|---|
| 6,254,639 B1 | 7/2001 | Peckitt | |
| 2005/0273165 A1* | 12/2005 | Griffiths | A61C 8/0006 623/16.11 |
| 2008/0228278 A1* | 9/2008 | Lee | A61C 8/0018 623/17.17 |
| 2013/0325129 A1 | 12/2013 | Huang | |
| 2015/0140511 A1 | 5/2015 | Ali | |
| 2015/0289979 A1* | 10/2015 | Gabele | A61L 27/446 623/23.54 |
| 2017/0165072 A1 | 6/2017 | Peng et al. | |
| 2020/0261229 A1* | 8/2020 | Dimitroulis | A61B 17/15 |

FOREIGN PATENT DOCUMENTS

| | | | |
|---|---|---|---|
| DE | 19915395 A1 * | 10/2000 | ............ A61B 17/86 |
| EP | 2730298 | 5/2014 | |
| JP | 2001-517972 | 10/2001 | |
| JP | 3184817 U | 6/2013 | |
| JP | 2015-507491 | 3/2015 | |
| RU | 2572355 | 1/2016 | |
| WO | 98/12995 | 4/1998 | |
| WO | 00/59409 | 10/2000 | |
| WO | 03/030787 | 4/2003 | |
| WO | WO 2012/118843 | 9/2012 | |
| WO | WG2013/00677 8 | 1/2013 | |
| WO | WO 2013/006778 | 1/2013 | |

OTHER PUBLICATIONS

German Search Report dated Mar. 1, 2018 from German Application No. 10 2017 115 403.5.
Chinese Office Action dated Mar. 17, 2021 from Chinese Application No. 201880045779.5.
European Office Action dated Oct. 5, 2021 from European Application No. 1 8 745 514.2.
Brazilian Office Action dated Apr. 27, 2022 from Brazilian Application No. BR112020000650-5.

* cited by examiner

BIORESORBABLE BONE IMPLANT AND PRODUCTION METHOD

The invention relates to a bone implant suitable for use as a filler for correcting an incorrect position of a bone, especially an incorrect jaw position, the implant having a first portion for attachment to a first bone portion of the bone and a second portion for attachment to a second bone portion of the bone, and the bone implant being prepared so that, when fixed to the bone, it orients the first bone portion and the second bone portion with respect to each other and keeps said portions at a distance from each other, thus predefining a volume. Further, the invention relates to a method for producing such a bone implant.

Bone implants are also used in so-called dysgnathias. A dysgnathia is understood to be a faulty development of the teeth, the jaws and/or the masticatory system which relates to the position of the teeth, the toothing, the jaw shape, the position of the jaws relative to each other or the incorporation of the jaws in the skull. Herefrom both esthetic and functional impairments in the jaw and facial area are resulting. Said incorrect positions may entail, inter alia, false loads of the temporomandibular joint with cracking and friction murmurs as well as complaints such as pain and restrictions of movement. However, the complaints may also extend beyond the jaw and facial area. These include painful tensions of the facial and masticatory muscles, gnashing or pressing to eliminate the incorrect tooth position or the incorrect jaw position, impairments of nasal respiration, drying of the oral cavity, complaints in the neck and shoulder muscles and chronical dorsal or neck pain. All of said complaints can be caused by the incorrect jaw position; therefore, it is common practice to eliminate the incorrect jaw position by surgical correction. The invention is located in this field.

There are plural types of the dysgnathia/incorrect jaw position. The jaws may be located too far in the front or too far in the rear, may deviate to the right or to the left or may be incorporated too high or too low in the facial bones. Accordingly, the rearward mandibular position in which the mandible is reset relative to the maxilla is the most frequent form of dysgnathia.

It is known from the state of the art to correct said incorrect jaw position by severing the jaw bone by an operative procedure and fixing the same at its new desired position by small titanium screws or titanium plates. In this respect, WO 97/01991 A1 discloses a bone-fragment fixing device comprising a longitudinal bone plate which comprises two continuous screw holes at each of its two ends, wherein (A) the bone plate has a central slot extending in the direction of the longitudinal axis of the plate; (B) a slide is provided which is disposed on the webs laterally delimiting the slot so as to be displaceable in the direction of the longitudinal axis of the plate; and (C) the slide has a slot extending transversely to the longitudinal axis of the plate in the mounted state. Hence, in this device the bone is severed, the two portions are positioned relative to each other and are attached at the desired position via plates or screws arranged from outside on the jaw.

In addition, WO 00/59409 A1 relates to a bone implant device serving as a spacer. Furthermore, RU 2 572 355 C1 discloses an individual implant which is identical to a cut-out segment of the jawbone. From WO 03/03787 A1, a method for manufacturing of patient-specific implants is known. Furthermore, WO 98/12995 A2 discloses an accurately fitting bone implant.

However, it is always a drawback of the state of the art that, on the one hand, fixation from outside on the bone is visible in the face and thus affects the esthetics of the patient. On the other hand, a second operative procedure is necessary to remove the fixing plate or the fixing screws again. Also, in this area of the severing an indentation remains evident, even when the latter is covered by skin. This is extremely poor in terms of esthetics. It is another drawback that the orientation of the two bone portions relative to each other is performed during the operative procedure and must be adjusted, e.g., via the slot. Consequently, the success of the operation and the esthetic and functional result are strongly dependent on the surgeon's skills.

Thus, it is the object of the invention to avoid or at least reduce the drawbacks from the state of the art. Especially a bone implant is to be provided which ensures an optimum surgical outcome and avoids a possible second procedure by the fact that the bone implant can be decomposed by the body and is transformed into a natural bone. Although bone regenerating products and bone replacement materials are known, they are provided as granules, curable cements or prefabricated molded bodies of simple geometry, however, so that they are inappropriate or usable at least to a restricted extent only for replacement as implants having an adapted shape and structuring.

The bone implant thus is intended to adopt plural functions. So, on the one hand, a gap is to be created during surgical displacement and subsequently is to be maintained, on the other hand, so that autologous bony replacement material can be positioned there in the healing process, especially is allowed to grow into/re-grow in said gap. For this purpose, the bone implant is designed as a filler which closes the gap between two bone portions (completely) separated from each other to fill the volume. During the healing process, said filler is replaced completely or at least predominantly by the body's own bone, as the latter grows into the filler while resorbing the same. Undesired anatomic deviations, such as subcutaneous dimples, are to be avoided.

According to a first aspect of the invention there is provided a bone implant suitable for use as a filler for correcting an incorrect position of a bone in the field of dysgnathia, the bone implant having a first portion for attachment to a first bone portion of the bone and a second portion for attachment to a second bone portion of the bone, the bone implant being prepared so that, when fixed to the bone, it orients the first bone portion and the second bone portion relative to each other and keeps said portions at a distance from each other, the bone implant having such geometry and being adapted such that the bone implant can be inserted between the first bone portion and the second bone portion so as to force a predetermined orientation of the second bone portion relative to the first bone portion.

According to the invention, the object of the invention is achieved by the fact that the bone implant has such geometry and is adapted such that the bone implant can be inserted between the first bone portion and the second bone portion so as to force a predetermined orientation of the second bone portion relative to the first bone portion. In other words, this means that the bone implant is not arranged from outside, viz. to be outwardly projecting, on the bone portions but is in the form of a spacer/gap filler/fill element/placeholder or bone wedge. The bone implant is thus inserted e.g. in the longitudinal direction of the bone. In other words, this also means that the bone implant is inserted at a position such that it replaces natural bone, i.e. it forms a bone piece which corrects the incorrect position. Consequently, the bone implant is not configured such that it constitutes a plate-shaped and/or external outer fixation for the two bone portions, but that it constitutes an internal fixation reproducing an original/desired shape of the bone. The bone implant according to the invention is configured so that the first and second bone portions are forced to be oriented when the implant is inserted, i.e. a position of the two bone portions need not necessarily be readjusted any longer manually, e.g. during the operative procedure. Of course, for specific difficult cases fine adjustment should still be possible.

This offers the advantage that, when implanting the bone implant, a forced orientation of the first bone portion and the second bone portion and, resp., of the position of the two portions opposed to each other is reached which corresponds to a desired optimum position. The position of the two bone portions thus need no longer be necessarily adjusted during the operative procedure so that, on the one hand, a better result can be achieved and, on the other hand, the operating time can be considerably reduced. If desired, however, an adjustment can be made.

In other words, a placeholder is used by which positional information is transmitted. The mechanical integrity of said placeholder ensures stable fixation.

Advantageous embodiments are claimed in the subclaims and shall be explained in detail hereinafter.

In addition, it is useful when the first portion is configured to abut on the first bone portion and the second portion is configured to abut on the second bone portion, the first portion being arranged to be opposed to the second portion. Opposed in this context means that the first portion is arranged at a first side/surface of the bone implant which is a side/surface of the bone implant different from a second side/surface on which the second portion of the bone implant is configured, with the first side and the second side being arranged diametrically relative to each other. By the bone implant abutting with the first side on the first bone portion and with the second side on the second bone portion, the geometry of the bone implant and the displacement of the bone portions relative to one another thus are defined. In particular, on the one hand, the distance (e.g. by the distance of the two sides from each other) between the two bone portions is corrected and, on the other hand, also a relative displacement (e.g. by inclination of the two sides relative to each other) is determined in the vertical direction, the longitudinal direction or the width direction.

It is especially advantageous when the geometry of the bone implant is adapted to the individual incorrect position of the bone, i.e. is configured corresponding to a correcting geometry, i.e. corresponding to a difference between the incorrect position and a desired position. This can also consist in or incorporate an over-correction, viz. can be such that the bone implant acting as a filler/placeholder projects from the bone. In this case, excessive osteolysis can be prevented. In this way, it can be determined in advance, viz. when the individual bone implant is created, in which way the dysgnathia is to be corrected.

Furthermore, it is preferred when the bone implant contains or is constructed from biodegradable metallic materials and/or contains or is constructed from resorbable polymers or ceramic materials. Especially magnesium, magnesium alloys, iron, iron alloys, barium and strontium stood the test. Among polymers and ceramics, also the composites thereof have stood the test. In this context, especially such materials as PDLLA, PLGA, PLA, PGA, chitosan fibers/particles, HAP, $CaCO_3$; alpha/beta TCP, hydroxy apatite and calcium phosphate, such as biphasic calcium phosphate (BCP) are worth mentioning. All biodegradable metallic materials and all resorbable polymers, ceramics and the composites thereof are basically suited, but all of them have specific benefits and peculiarities. $Ca_3(PO_4)_2O_3$ is equally suited just as mixtures of beta-TCP and hydroxy apatite. The use of singular addition of HA in said materials is imaginable as well.

It is also advantageous when the filler comprises calcium and phosphate, as the natural bone mostly consists of calcium phosphate so that synthetic calcium phosphate compounds constitute suitable bone replacement materials.

In addition, it is of advantage when the bone implant comprises tricalcium phosphate ($Ca_3(PO_4)_2$). Especially said materials have turned out to be suited for forming a bioresorbable bone implant. Tricalcium phosphate is frequently used as bone replacement material and bone augmentation material.

Further preferred, the bone implant may comprise β-tricalcium phosphate (β-TCP), as this material exhibits suitable properties inter alia regarding shape, structure, bioresorbability, tolerance and strength.

It is also possible that the bone implant comprises α-tricalcium phosphate (α-TCP), hydroxy apatite (HA) and/or a mixture of β-tricalcium phosphate (β-TCP) and hydroxy apatite (biphasic calcium phosphate, abbreviated to BCP).

Also, blood products (PRP), cells and/or biologically active molecules such as e.g. proteins, peptides or DNA, RNA and/or oligonucleotides can be used.

In order to obtain a stable insertion product, it has proven its worth when the bone implant in the form of a filler at least in portions has a truss-type or grid-type structure. Advantageously, a closed or broken edge may surround the outside of the truss-type or grid-type structure.

When the webs are joined on top of and/or are joined next to one another to provide a three-dimensional structure, a voluminous filler abutting on all intersections and fitting in terms of volume can be used which also has an initial minimum strength predestined for trouble-free use.

For enabling a structure well-suited for bone growth which is sufficiently strong to be used, it is constructive when the webs extend to be inclined relative to one another, approximately orthogonally, and have contacting and connecting areas at which a single-material transition is created from one web to the other and/or to the edge.

It is advantageous when at least one cavity is formed between the webs.

An advantageous example embodiment is also characterized in that a plurality of cavities is provided in predefined areas at a distance from the webs.

A web can be configured so that it defines a hole having a preferably closed hole wall. Alternatively or additionally, at the web also a handle may be provided for the surgeon, for example in the form of a pin, a cylinder. In the handle a predetermined breaking point may be present, preferably following the surface of the filler, especially of a web provided on the outside. The webs may extend in a strand-type manner or as strands. They may be straight or curved. A zigzag pattern is also imaginable. In the case of a bend or a curvature, a constant bend/curvature or a bend/curvature increasing/decreasing over the length can be realized, which may entail benefits in terms of strength.

A web may be in the form of a dense ball package, the adjacent cavities being shaped by the missing of "balls". The web may be structured by particles/powders/granules/lumps and fractions therefrom at a size/a (mean) diameter of from 1 μm to 100 μm.

It is further advantageous when the bone implant is in the form of a massive implant, i.e. a tight solid implant which is formed substantially without any recesses and air inclusions, and/or as a (micro-/macro-) structured or porous implant, i.e. an implant having a grid structure and/or plural recesses and/or air inclusions. Depending on the use, various advantages thus can be provided for the bone implant. Especially, in this way the resorption rate/the strength and the weight of the bone implant can be appropriately influenced.

The recesses and the grid structures/webs/strands simultaneously enable blood-based products and/or proteins to be absorbed, such as of growth factors and/or cellular systems such as autologous/analogous or heterologous cells/stem cells. Due to the particular hydrophilic property of the implant produced, it comes to a quick reaction between said components and the implant structure, which later will result in improved clinical results.

Further, it is useful when the bone implant is made from composed layers and/or is produced in a generative manufacturing method. So, the individual bone implant can be generated especially quickly and subsequently can be joined to form a composite bone implant. The function of the bone implant is not impaired.

A preferred example embodiment excels by the fact that the bone implant comprises an organic matrix including ceramic particles (slurry).

Especially the particles are preferred to form a homogenous dispersion, i.e. to be evenly distributed in the matrix. In this way, the bone implant exhibits equal or similar structural properties across the entire shape.

Also, the organic matrix including the ceramic particles (between 1 and 100 μm) can be cured e.g. by selective light exposure such as digital light processing (DLP). In this way, an especially tight structure of the bone implant is produced. It is also possible to use a different thermal treatment process for increasing the strength.

It is further advantageous when the individual layers are cured, as this results in an especially uniform distribution of hardness and the curing process thus can be accelerated.

Furthermore, it is of advantage when the bone implant is produced in a generative manufacturing process. This helps to individually create the bone implant on the basis of a calculated model. Since in a generative/additive method, such as e.g. 3D printing, laser sintering, sandwich technologies, an implant can be produced directly from a computer model, it is avoided that a separate mold or the like has to be produced for each patient and thus for each individual bone implant.

According to a second aspect of the invention there is provided a method for producing a bone implant according to the first aspect of the invention, wherein the jaw anatomy/bone anatomy of the patient is detected in one step, wherein then in one step a geometry of the bone implant is calculated for correcting an incorrect position of a bone and is generatively/additively manufactured. Of preference, the cured bone implant is lifted bit by bit out of the bed during curing, with new particles within a fluid being resupplied to beneath the already partially cured bone implant and being cured there again by irradiation such as by a laser.

Hereinafter, the invention will be illustrated by way of drawings, wherein.

The figures are merely schematic and serve exclusively for the comprehension of the invention. Like elements are marked by like reference numerals. The different features of the individual example embodiments may be interchanged at will.

Figure 1:
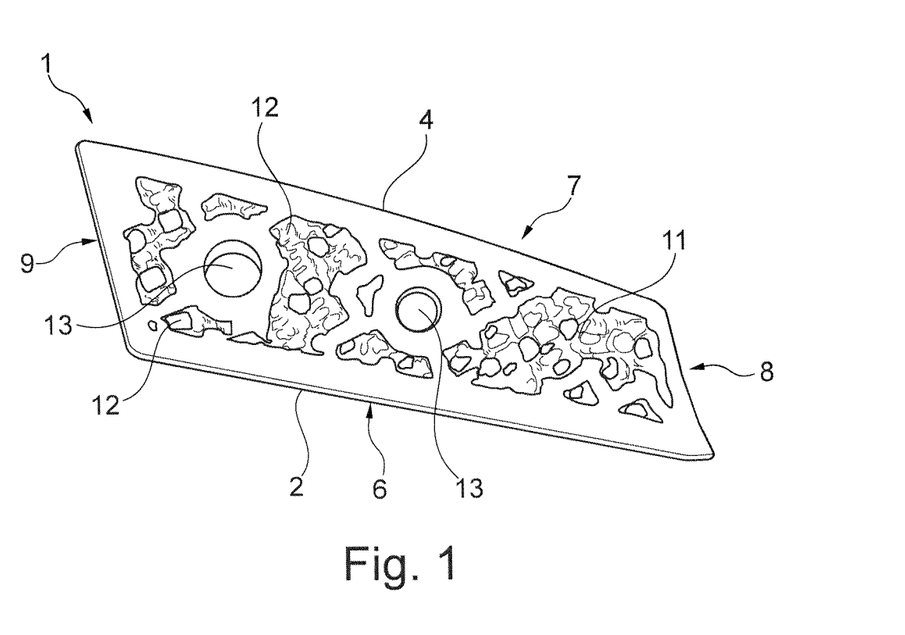
FIG. 1 shows a perspective view of a bone implant according to the invention in a first example embodiment.

FIG. 1 illustrates a bone implant 1 which is used as a filler for filling a gap in the bone when correcting an incorrect position of a bone, especially an incorrect jaw position, in the field of dysgnathia. The bone implant 1 has a first portion 2 for attachment to a first bone portion 3 of the bone and a second portion 4 for attachment to a second bone portion 5 of the bone. The bone implant 1 is prepared so that, when fixed to the bone, it orients the first bone portion 3 and the second bone portion 5 relative to each other and keeps said portions at a distance from each other. The bone implant 1 thus has such geometry which is adapted such that the bone implant 1 can be inserted between the first bone portion 3 and the second bone portion 5. Consequently, when inserting the bone implant 1, a predetermined orientation of the second bone portion 5 relative to the first bone portion 3 is forced.

The first portion 2 of the bone implant 1 is formed at a first surface 6 of the bone implant and the second portion 4 of the bone implant 1 is formed at a second surface 7. The two surfaces 6, 7 are arranged to be opposed to each other. Further, on a lower side the bone implant 1 includes a surface 8 and on an upper side the bone implant 1 includes a surface 9 which, in the inserted condition, fit into the contour of the bone. The bone implant/implant 1 from FIG. 1 takes a substantially rectangular shape. However, the shape of the implant 1 may strongly vary depending on the incorrect bone position.

Figure 2:
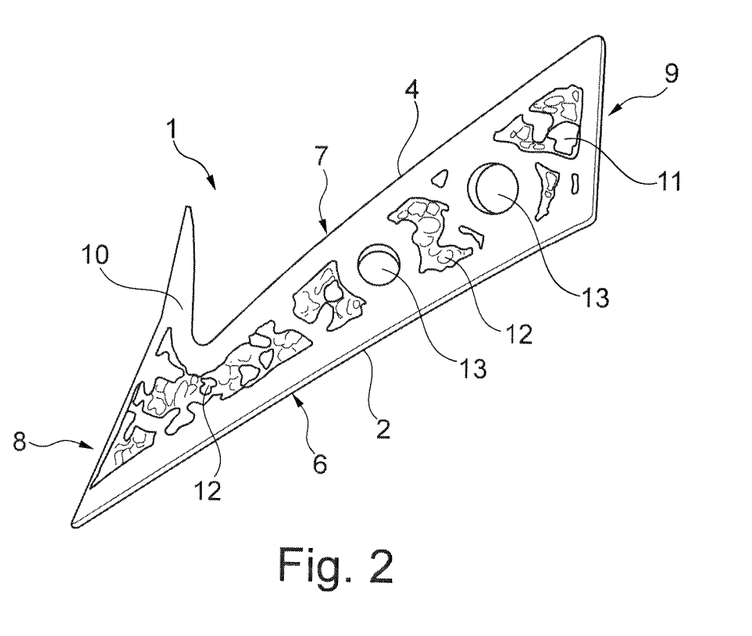
FIG. 2 shows a perspective view of the bone implant in a second example embodiment.

The implant 1 from FIG. 2 takes a "1" shape or the shape of a hook having a pointed projection 10 protruding in the direction of the second side 7. In the inserted condition, the second bone portion 5 abuts on the second side 7 and on the inner side of the projection 10. The outer side of the projection 10 is formed by the surface 8.

Both in the implant 1 from FIG. 1 and in the implant 1 from FIG. 2, the first surface 6 and the second surface 7 are inclined toward each other so that the use of the implant 1 helps to achieve both a spacing of the two bone portions 3, 5 and a relative rotation.

Figure 3:
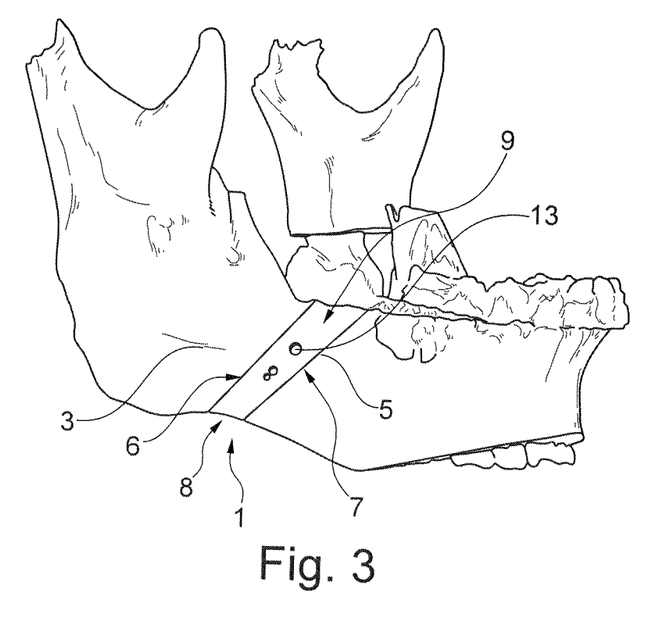
FIG. 3 shows a perspective representation of the bone implant in the first example embodiment in the implanted condition in connection with a mandible.
Figure 4:
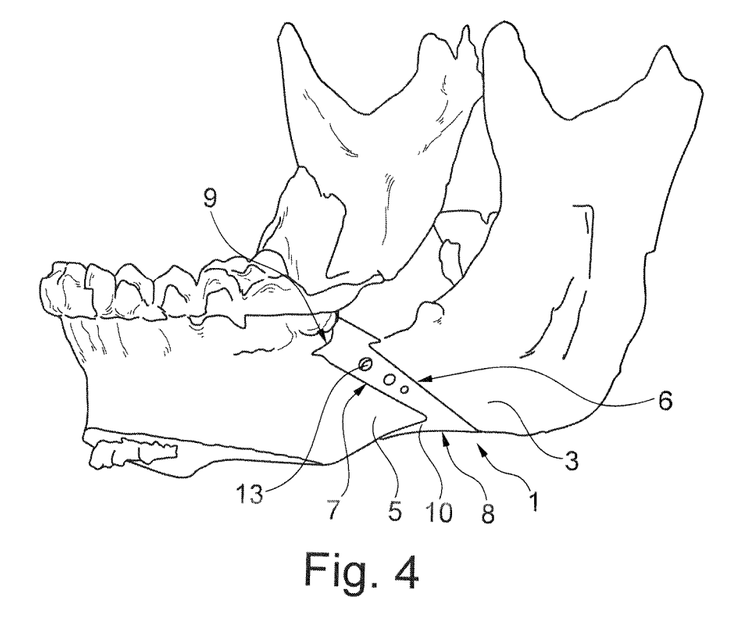
FIG. 4 shows a perspective view of the bone implant in the second example embodiment in the implanted condition in connection with the mandible.

In FIG. 3 and, resp., FIG. 4, the implants from FIG. 1 and, resp., FIG. 2 are shown in a condition inserted in the jaw. The first and, resp., second surfaces 6, 7 of the bone implant 1 abut to be flush with the first and, resp., second bone portions 3, 5. The bone implant 1 may be designed to have a grid structure 11 (cf. FIG. 1 or FIG. 2) so that it forms a type of porous implant having plural recesses 12 or may be designed as a solid implant (cf. FIG. 3 or FIG. 4).

The bone implant includes plural recesses in the form of a through-bore 13 which are used for fixation by fasteners (not shown). The through-bores 13 are configured in a direction which is perpendicular to the longitudinal direction of the bone implant 1 and thus also perpendicular to the longitudinal direction of the bone.

Figure 5:
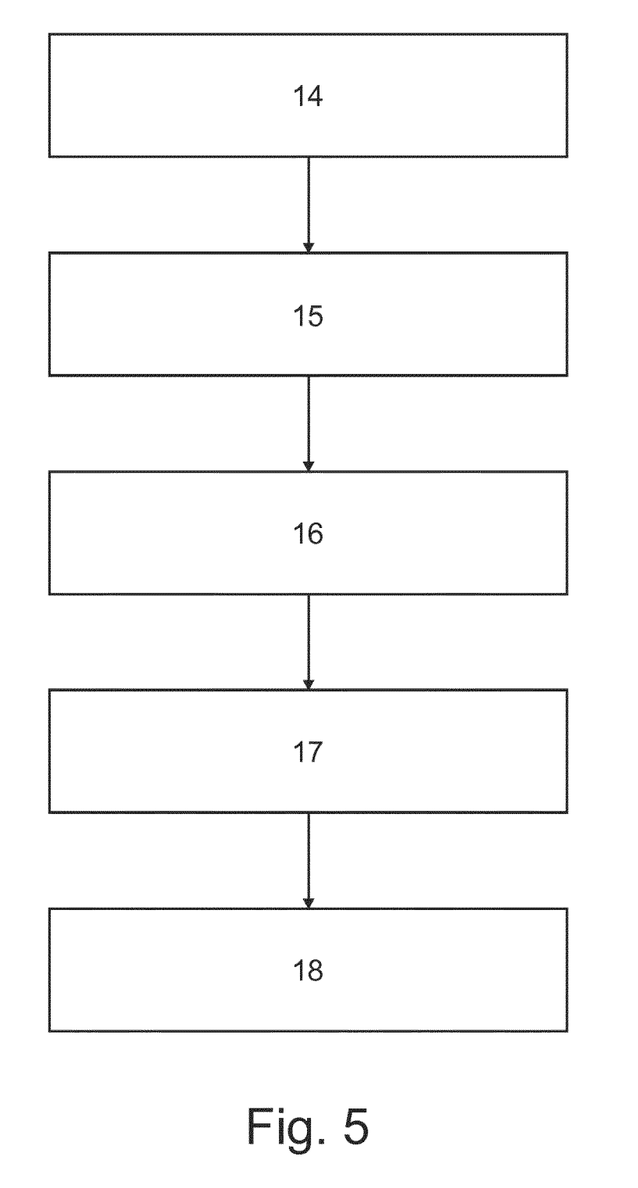
FIG. 5 shows a schematic representation of the method steps of a method for producing the bone implant.

FIG. 5 illustrates the process steps of a method for producing such bone implant 1. In a first step 14 the jaw anatomy/bone anatomy of a patient is detected e.g. by computer tomography. In a second step 15, a geometry of the bone implant 1 is calculated for correcting the incorrect position of the bone. Inter alia, an intersection line for severing the bone is determined and the geometry, especially that of the first portion 2 and that of the second portion 4, is adapted to the intersection line. Subsequently, in a third step 16 the geometry of the (calculated) bone implant 1 is broken down into very thin and defined layers. In a subsequent fourth step 17, the layers are produced e.g. in a generative manufacturing method and optionally the strength thereof is additionally increased by a heat treatment. After that, in a fifth step 18 the layers are stacked one on top of the other and are connected to one another so that a bone implant is formed.

LIST OF REFERENCE NUMERALS

1 bone implant/implant
2 first portion
3 first bone portion
4 second portion
5 second bone portion
6 first surface
7 second surface
8 surface
9 surface
10 projection
11 grid structure
12 recess
13 through-hole
14 first step
15 second step
16 third step
17 fourth step
18 fifth step

The invention claimed is:

1. A bone implant suitable for use as a filler for orienting a position of a bone for correcting the position of the bone in the field of dysgnathia, the bone comprising a first bone portion and a second bone portion separated by a gap, the bone implant having a first portion having a first surface for attachment to the first bone portion of the bone and a second portion having a second surface for attachment to the second bone portion of the bone, wherein the first portion is arranged at a first side of the implant and configured to abut on the first bone portion and the second portion is arranged at a second side of the implant configured to abut on the second bone portion, the first portion being arranged to be opposed to the second portion, the first surface being on an opposing end of the bone implant and at a predetermined distance and orientation from the second surface so that, when the bone implant is fixed to the bone, it orients the first bone portion and the second bone portion relative to each other and keeps said portions at a distance from each other, the bone implant having such geometry and being adapted such that the bone implant can be inserted in the gap between the first bone portion and the second bone portion, wherein the bone implant is formed as a three-dimensional structure having a mechanical integrity such that the first surface of the first portion is configured to abut on the first bone portion and the second surface of the second portion is configured to abut on the second bone portion to force a predetermined orientation between the first bone portion and the second bone portion to orient the second bone portion relative to the first bone portion to the predetermined orientation upon insertion of the bone implant in the gap to fill the gap and permanently fix the first bone portion to the second bone portion at the predetermined orientation and wherein the implant has the shape of a hook having a pointed projection protruding in the direction of the second side.

2. The bone implant according to claim 1, wherein the first surface is inclined with respect to the second surface so as to force a predetermined angular orientation of the second bone portion relative to the first bone portion.

3. The bone implant according to claim 2, wherein the bone implant contains or is made up from biodegradable metallic materials and/or contains or is made up from resorbable polymers or ceramic materials.

4. The bone implant according to claim 1, the bone implant contains or is made up from biodegradable metallic materials and/or contains or is made up from resorbable polymers or ceramic materials.

5. The bone implant according to claim 1, wherein the bone implant in the form of a filler at least in portions has a truss-type or grid-type structure.

6. The bone implant according to claim 5, wherein the truss-type or grid-type structure comprises webs that are joined on top of one another and/or are joined next to one another to create a three-dimensional structure.

7. The bone implant according to claim 6, wherein the webs extend to be inclined relative to one another and have contacting and connecting areas.

8. The bone implant according to claim 7, wherein at least one cavity is formed between the webs.

9. The bone implant according to any one of the claim 6, wherein at least one cavity is formed between the webs.

10. The bone implant according to claim 6, wherein a plurality of cavities is present in predefined areas at a distance from the webs.

11. The bone implant according to claim 1, wherein the bone implant is constructed of composite layers and/or is produced in a generative manufacturing method.

12. A method of producing a bone implant according to claim 1, wherein a geometry of the bone implant is calculated in one step for correcting an incorrect position of a bone and is generatively produced.

13. The bone implant according to claim 1, wherein the bone implant when inserted in the gap between the first bone portion and the second bone portion forms a permanent internal fixation reproducing an original shape of the bone.

14. The bone implant according to claim 13, wherein the bone implant comprises a lower side having a lower surface spanning the first surface and second surface and an opposing upper side having an upper surface spanning the first surface and second surface, wherein one or more of the upper and lower surfaces fit into a contour of the bone when the bone implant is inserted.

15. The bone implant according to claim 1, wherein the first portion is fixed to the first bone portion and the second portion is fixed to the second bone portion, without having fastening plates protruding laterally from the first portion of the bone implant, the second portion of the bone implant, the first bone portion and the second bone portion.

* * * * *